United States Patent [19]
Ligtenberg et al.

[11] Patent Number: 5,997,570
[45] Date of Patent: Dec. 7, 1999

[54] METHOD FOR INTRODUCING A CURABLE STENT USING CATHETER WITH LIGHT CONDUCTOR

[75] Inventors: Hendrikus Cornelis Geert Ligtenberg, Leek; Marcel Gerhard Haan, Roden, both of Netherlands; James Ernest Leone, Miami, Fla.

[73] Assignee: Cordis Corporation, Miami Lakes, Fla.

[21] Appl. No.: 08/926,137

[22] Filed: Sep. 9, 1997

Related U.S. Application Data

[63] Continuation of application No. 08/613,889, Mar. 11, 1996, abandoned.

[30] Foreign Application Priority Data

Mar. 13, 1995 [NL] Netherlands ............................ 9500493

[51] Int. Cl.[6] ....................................................... A61N 1/30
[52] U.S. Cl. ................................ 607/92; 606/13; 606/14; 606/15; 606/16; 604/96
[58] Field of Search ..................................... 606/2, 13, 14, 606/15, 16, 7, 8, 191, 192, 194, 195; 604/96; 607/92

[56] References Cited

U.S. PATENT DOCUMENTS

| | | |
|---|---|---|
| 4,643,186 | 2/1987 | Rosen et al. ............................. 607/156 |
| 4,773,899 | 9/1988 | Spears . |
| 4,860,743 | 8/1989 | Abela ........................................... 606/7 |
| 4,878,492 | 11/1989 | Sinofsky et al. . |
| 5,100,429 | 3/1992 | Sinofsky et al. . |
| 5,267,081 | 11/1993 | Pein .......................................... 359/584 |
| 5,344,419 | 9/1994 | Spears .......................................... 606/7 |
| 5,354,774 | 10/1994 | Deckelbaum et al. . |
| 5,370,608 | 12/1994 | Sahota et al. . |
| 5,514,669 | 5/1996 | Selman ....................................... 514/63 |

FOREIGN PATENT DOCUMENTS

| | | |
|---|---|---|
| 0 646 360 A1 | 10/1994 | European Pat. Off. . |
| WO 83/03188 | 9/1983 | WIPO . |

*Primary Examiner*—Linda C. M. Dvorak
*Assistant Examiner*—Rosiland Kearney
*Attorney, Agent, or Firm*—Gerstman, Ellis & McMillin, Ltd.

[57] ABSTRACT

A method is disclosed for introducing a stent inside the body of a patient. The stent is made of a material that cures due to the action of light. A catheter having an inflatable balloon adjacent its distal end is provided. Also provided is a light conductor comprising a transparent, elongated member, the elongated member having a smooth, outer wall along most of its length with a portion of the light conductor within the balloon having a rougher outer wall to allow light to project laterally outwardly through the wall. The balloon carries on substantially its entire surface a partially reflective layer to permit the light to be partly reflected and partly transmitted through the same portions of the wall of the balloon. The stent is cured by providing light to the light conductor.

8 Claims, 1 Drawing Sheet

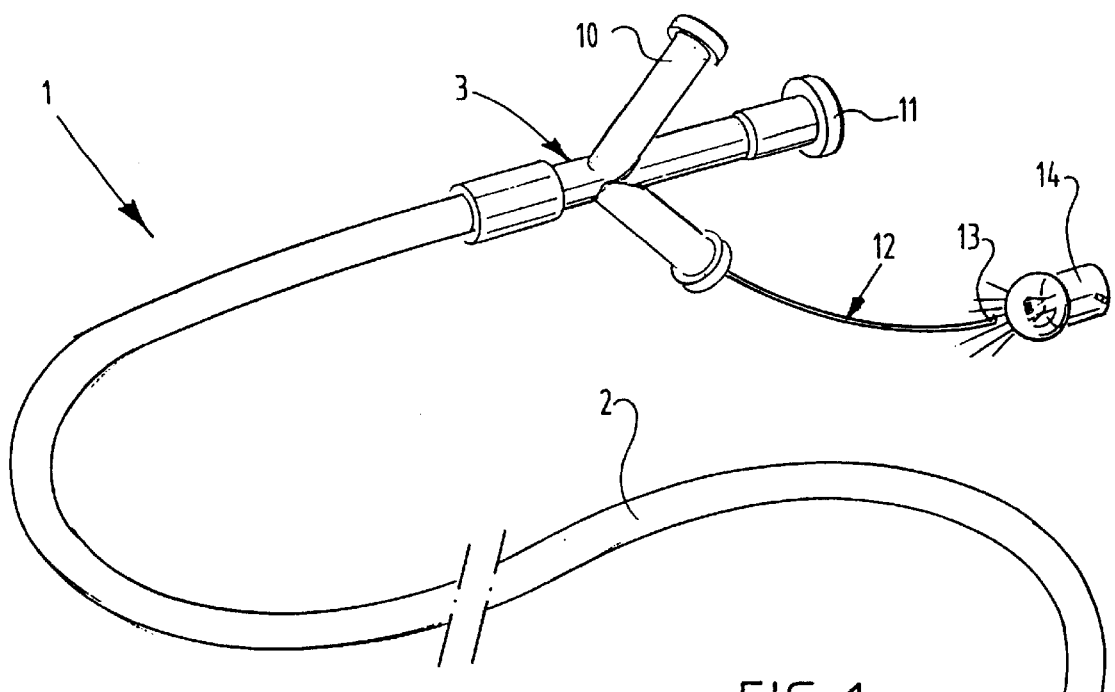
FIG. 1
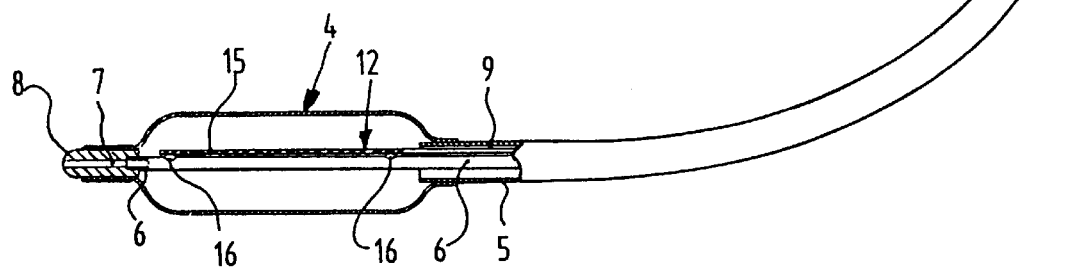
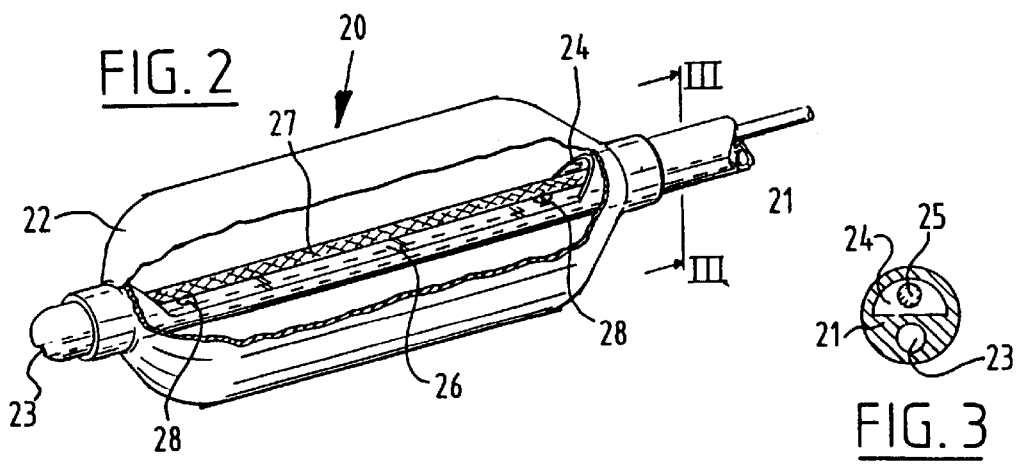

METHOD FOR INTRODUCING A CURABLE STENT USING CATHETER WITH LIGHT CONDUCTOR

This is a continuation of U.S. application Ser. No. 08/613,889, filed Mar. 11, 1996, now abandoned.

BACKGROUND OF THE INVENTION

In International Publication WO83/03188; Sinofsky et al. U.S. Pat. No. 4,878,492; and the like, balloon catheters are disclosed which carry an optical fiber for permitting irradiation in the region of the balloon. Such balloon catheter devices have been used for the placement of a Glastra stent, which stent may be expanded by a balloon catheter in the blood vessel of a patient or other desired location, and then cured with ultraviolet light so that the stent cures to rigidity.

Optical fibers of the prior art may be quartz fibers, but deliver the ultraviolet light within the catheter from the distal end of the fiber in the form of a light cone. By this invention, an optical fiber is provided for a catheter in which the light is delivered radially over a desired length of the fiber. Thus, a system may be provided in which an optical fiber is secured inside of a catheter balloon providing radial light delivery without the risk of balloon puncture with the sharp fiber end.

DESCRIPTION OF THE INVENTION

The invention relates to a catheter comprising in the usual manner a tube-like basic catheter body with a distal and a proximal end. A balloon member is carried on the distal end.

The balloon member surrounds an end-section of the basic body and is supported by it.

A light conductor extends from the proximal end to the distal end of the basic body. This light conductor comprises a light-emitting end-section which is situated inside the balloon member. The light-emitting end-section is attached to the basic body inside the balloon member, in order to secure it inside the balloon.

At the proximal end of the catheter, the light conductor defines a light-absorbing end, into which light can be received. This light is then emitted at the light-emitting end section inside the balloon.

This balloon catheter according to the invention is particularly suitable for carrying a stent which has been made of a material that cures due to the action of light, particularly UV-light, inside the body of a patient. Prior to introduction, this stent is arranged in compressed state around the non-expanded balloon member. In this state, the distal end of the catheter is inserted into the patient, after which the balloon and consequently the stent are manoeuvred into the correct position inside typically the bloodstream of the patient. By subsequently causing the balloon member to expand by supplying gas or liquid under pressure to it, the stent will also be expanded. By next exposing the stent thus introduced to light emitted by the light-emitting end-section of the light conductor, the material of which the stent has been made will cure and the expanded stent will subsequently remain behind in the cured, expanded state inside the body of the patient.

It is important that the light-emitting end-section is positioned accurately inside the balloon member, in order to achieve an accurate and correct exposure of the curing material.

According to a preferred embodiment, the basic catheter body comprises an outer tube-like member, and an inner tube-like member carried in a lumen thereof. The light-emitting end-section of the light conductor is fixed to the inner tube-like member. Together with the inner tube-like member, the light conductor extends through the lumen of the outer tube-like member.

The light-emitting end-section can thus be fixed accurately inside the balloon. By removing at least a section of the wall of the inner tube member adjacent the end section, a kind of bed is obtained which can contribute to keeping the light conductor end-section in place on introduction.

The light conductor is preferably fixed to the basic body by gluing.

In order to ensure that all around the circumference of the balloon a uniform exposure is achieved, the light emitted by the light conductor may be partly reflected inside the balloon. As a result also that side of the balloon which is situated in the shade cast by, the basic body can be properly exposed to irradiation.

Preferably, the light conductor comprises a transparent elongated member such as one or more quartz fibers, or a tube of transparent material, which may be made of braided transparent fibers if desired. The light conductor extends within the basic catheter body typically from the proximal catheter end to a distal position within the balloon. The light conducting elongated member has a smooth outer wall or walls (if plural members are present) along most of the length of the light conducting member, to prevent light leakage through the smooth wall by principles of light conducting that are well known. However, a portion of the light conductor within the balloon has an outer wall of an elongated member which carries a rougher surface than the smooth wall, with the effect that light can project laterally outwardly through the wall in this section because of the roughness of the surface. Thus, light is conveyed through the catheter to the distal area which is typically surrounded by a balloon, without major light loss, then, the light is emitted laterally (radially) outwardly from the light conductor. The light can pass through the balloon to irradiate a stent carried by the balloon in the manner described above, or the light may be used for other purposes if desired.

It may be also desirable to provide a partially reflective characteristic to the inner surface of the balloon by conventional means such as the partial application of an extremely thin titanium dioxide or metallic film (silver or aluminum), or the like. Thus, part of the light may be reflected from the inner balloon walls back to other portions of the balloon walls, to provide more uniformity of light emission within and through the balloon walls, particularly if the light conductor is supported by the inner tube-like member as described above so that a shadow is cast in some radial directions.

The invention will be explained in greater detail in the following description with reference to the attached drawings.

DESCRIPTION OF THE DRAWINGS

FIG. 1 shows partly schematically a balloon catheter according to a first embodiment of the invention;

FIG. 2 illustrates the distal end of a balloon catheter according to another embodiment of the invention; and FIG. 3 shows a cross-section along the line III—III of FIG. 2.

DESCRIPTION OF A PREFERRED EMBODIMENT

The catheter 1 of FIG. 1 comprises a tube-like basic catheter body 2 with a proximal end, that is to say the end which remains outside the body of a patient during treatment, which carries a connecting member 3.

At the opposite, distal end, a balloon member 4 is carried in conventional manner, surrounding an end-section of the basic body 2.

The basic body comprises an outer tube-like body 5 and an inner tube-like body 6 received in a lumen 9 of outer body 6. The inner tube-like body 6 also comprises a lumen 7, through which a guidewire can extend in the usual manner.

At its tip, the inner tube-like body 6 is connected with a catheter-end-section 8, inside of which the guidewire channel 7 is continued.

The balloon member 4 is connected with its distal end to the catheter-end-section 8 and with its proximal end to the end of the outer tube-like body 5.

A light conductor 12 extends together with the inner tube-like body 6 through the lumen 9 of the outer tube-like body 5. Light conductor 12 extends from the proximal catheter end toward the distal end, terminating within balloon 4, where conductor section 15 is situated inside the balloon member 4 in an uncovered state.

Light conductor 12 comprises an optical cable in which a quartz or other transparent fiber or fibers are provided, having smooth walls in conventional manner so that light travels along the cable and is not lost by laterally scattering out of the cable. However, in conductor section 15, the uncovered light conducting member or members define the roughened surface previously described so that they emit light laterally outwardly toward the wall of balloon 4, to provide irradiation through the balloon wall to a stent carried by the balloon, or for any other desired purpose.

The proximal end-section of light conductor 12 comprises a light-absorbing end 13 through which, by means of a schematically indicated source of light 14, light can be admitted into the light conductor 12. This light is transmitted inside light conductor 12 to the light-emitting end-section 15. As stated above, this light-emitting end-section 15 has preferably been treated in such a way, for instance by grinding or treatment with HF, to produce the roughened surface so that admitted light is emitted radially along the entire end-section 15. End-section 15 is connected with the basic catheter body 2, and in particular with its inner tube-like body 6, by means of glued joints 16.

The balloon member 4 has preferably been treated on its inner surface, such as by partial silver application or aluminization, so that the light emitted by the light-emitting end-section 15 is partly reflected and partly transmitted. As a result of the partial reflection, the entire circumference of the inside of the balloon member 4 will be exposed more uniformly including that section which is situated in the direct shadow cast by inner body 6, found the bottom section of balloon 4 in FIG. 1. A uniform exposure of the entire circumference of the balloon 4 is desirable in order to effect uniform exposure of the stent to be cured.

The balloon member 4 is expanded by supplying liquid or gas under pressure to it. For this purpose the remaining cross-section of the lumen 9 is used surrounding inner body 6. This passageway is conventionally connected to the connector 10 of connecting member 3. Connecting member 11 connects with the guidewire channel 7. This connection 11 carries a conventional seal so that the guidewire can be advanced in a sealed manner.

In another embodiment of the catheter, as indicated in FIG. 2, with the reference number 20, only the distal end-section has been illustrated. Catheter 20 comprises a basic catheter body 21, which, as can be seen more clearly in FIG. 3, comprises two lumens 23, 24. The lumen 23 extends to the very distal end and serves for receiving a guidewire.

A light conductor 25 extends through lumen 24.

As can be seen in FIG. 2, the outer wall of the end-section of the basic body 21 extending inside the balloon member 22 and surrounding lumen 24 has been partially removed, so that a "bed" 26 is formed on which the light-emitting end-section 27 of the light conductor 25 is fixed. Also in this case glue spots 28 are used for the purpose of fixing.

Also the light-emitting end-section 27 has been treated with a roughened surface in such a way that a lateral or radial emission of light is effected in order to obtain a more uniform exposure along the entire length.

The light conductor can be made of a light-conducting monofilament or a fibre bundle. Also a combination can be employed. Light-emitting end-section 27 can for instance consist of one piece, which has been connected in a light transmitting manner with a fibre bundle extending from a proximal end.

The above has been offered for illustrative purposes only, and is not intended to limit the scope of the invention of this application, which is as described in the claims below.

What is claimed:

1. A method for introducing a stent inside the body of a patient, which comprises the steps of:

providing a stent made of a material that cures due to the action of light;

providing a catheter which defines a tubular basic catheter body, a distal end, a proximal end, and an inflatable balloon carried on said basic catheter body adjacent said distal end;

providing a light conductor which comprises a transparent, elongated member, said light conductor extending within said basic body from the proximal catheter end to a distal portion within said balloon, said elongated member having a smooth, outer wall along most of its length to prevent light leakage through said smooth wall, a portion of said light conductor within said balloon having a rougher outer wall to allow light to project laterally outwardly through said wall, said balloon being transparent, but carrying on substantially its entire surface a partially reflective layer to permit said light to be partly reflected and partly transmitted through the same portions of the wall of said balloon, whereby an improved uniformity of irradiation through the wall of the balloon is provided;

arranging the stent in a compressed state around the inflatable balloon while the balloon is in a non-inflated state;

inserting the distal end of the catheter into the patient;

maneuvering the balloon with stent into a desired position within the patient;

inflating the balloon to expand the stent; and curing the stent by providing light to said light conductor to expose the stent to light emitted by the light projected laterally outwardly through said outer wall.

2. The method of claim 1 in which the partially reflective layer carried on said transparent balloon comprises titanium dioxide or a metallic film.

3. The method of claim 1 in which said light conductor extends from the proximal to the distal end, said portion inside the balloon member being fixed to the basic body.

4. The method of claim 1 in which basic catheter body comprises an outer tube-like body and an inner tube-like body received in a lumen thereof, and the light-emitting portion of the light conductor is fixed to the inner tube-like body.

5. The method of claim 4 in which the light conductor extends, together with the inner tube-like body, through the lumen of the outer tube-like body.

6. The method of claim 1 in which the light conductor extends through a lumen of the basic body and in which an outer wall of a distal end-section of the basic body residing in the balloon member and surrounding the lumen has partially been removed.

7. The method of claim 3 in which the light conductor is affixed to the basic body by means of gluing.

8. A method for introducing a stent inside the body of a patient, which comprises the steps of:

providing a stent made of a material that cures due to the action of light;

providing a catheter which defines a tubular basic catheter body, a distal end, a proximal end, and an inflatable balloon carried on said basic catheter body adjacent said distal end;

providing a light conductor which comprises a transparent, elongated member, said light conductor extending within said basic body from the proximal catheter end to a distal position within said balloon, the catheter basic body comprising an outer tube-like body and an inner tube-like body received in a lumen of said outer tube-like body, said light conducting elongated member having a smooth, outer wall along most of its length to prevent light leakage through said smooth wall, a portion of said light conductor within said balloon having a rougher outer wall to allow light to project laterally outwardly through said outer wall, said inner-tube-like body and said light conductor extending through the lumen of said outer tube-like body, an outer wall of a distal end-section of the inner tube-like body positioned in said balloon having been partially removed to expose said portion of said light conductor, said balloon having a partially reflective wall at substantially its entire surface, whereby an improved uniformity of irradiation through the wall of the balloon is provided to permit light emitted from said light emitting portion to be partly reflected and partly transmitted through the same portion of the balloon wall;

arranging the stent in a compressed state around the inflatable balloon while the balloon is in a non-inflated state;

inserting the distal end of the catheter into the patient;

maneuvering the balloon with stent into a desired position within the patient;

inflating the balloon to expand the stent; and curing the stent by providing light to said light conductor to expose the stent to light emitted by the light projected laterally outwardly through said outer wall.

* * * * *